United States Patent [19]

Forte et al.

[11] Patent Number: 4,690,733
[45] Date of Patent: Sep. 1, 1987

[54] PROCESS FOR THE SEPARATION OF HYDROCARBONS FROM A MIXED FEEDSTOCK

[75] Inventors: Paulino Forte, Yonkers; Jose A. Vidueira, White Plains, both of N.Y.

[73] Assignee: Union Carbide Corporation, Danbury, Conn.

[21] Appl. No.: 794,845

[22] Filed: Nov. 4, 1985

[51] Int. Cl.$^4$ .................. B01D 3/38; B01D 11/00
[52] U.S. Cl. .................. 203/21; 203/96; 203/DIG. 8; 203/DIG. 14; 203/DIG. 25; 208/321; 208/353; 208/356; 208/363
[58] Field of Search .......... 203/DIG. 14, DIG. 8, 203/21, 25, 100, 96, DIG. 25, 91, 92, 95; 208/356, 353, 363, 321

[56] References Cited

U.S. PATENT DOCUMENTS

| | | | |
|---|---|---|---|
| 2,032,666 | 3/1936 | Roberts | 208/353 |
| 2,127,004 | 8/1938 | Nelson | 203/21 |
| 3,248,304 | 4/1966 | Goeldner | 203/21 |
| 3,421,567 | 1/1969 | Hoppe | 208/321 |
| 3,714,033 | 1/1973 | Somekh et al. | 208/321 |
| 3,714,034 | 1/1973 | Kosseim et al. | 208/321 |
| 3,779,904 | 12/1973 | Kubek et al. | 208/333 |
| 4,213,830 | 7/1980 | Köppl | 203/25 |
| 4,260,476 | 4/1981 | Vidueira et al. | 208/363 |
| 4,306,942 | 12/1981 | Brush et al. | 203/23 |
| 4,405,409 | 9/1983 | Tusel et al. | 203/21 |
| 4,410,400 | 10/1983 | Preusser et al. | 203/25 |
| 4,420,373 | 12/1983 | Egosi | 203/25 |
| 4,438,730 | 3/1984 | Link et al. | 203/DIG. 14 |

*Primary Examiner*—Kenneth M. Schor
*Assistant Examiner*—V. Manoharan
*Attorney, Agent, or Firm*—M. N. Reinisch

[57] ABSTRACT

In a combination solvent extraction-steam distillation process for the recovery of aromatic hydrocarbons, the improvement comprising (a) introducing high pressure steam into a steam ejector;

(b) passing the steam from step (a) to a first heat exchanger where it exchanges heat with cooler lean solvent coming from the bottom of the distillation column and is condensed;

(c) returning the lean solvent from step (b) to the bottom of the distillation column;

(d) passing part of the condensate from step (b) to a second heat exchanger where it exchanges heat with the warmer lean solvent coming from the bottom of the distillation column, cooling the lean solvent and vaporizing the condensate; and (e) passing the vapor from step (d) to the steam ejector in step (a).

2 Claims, 1 Drawing Figure

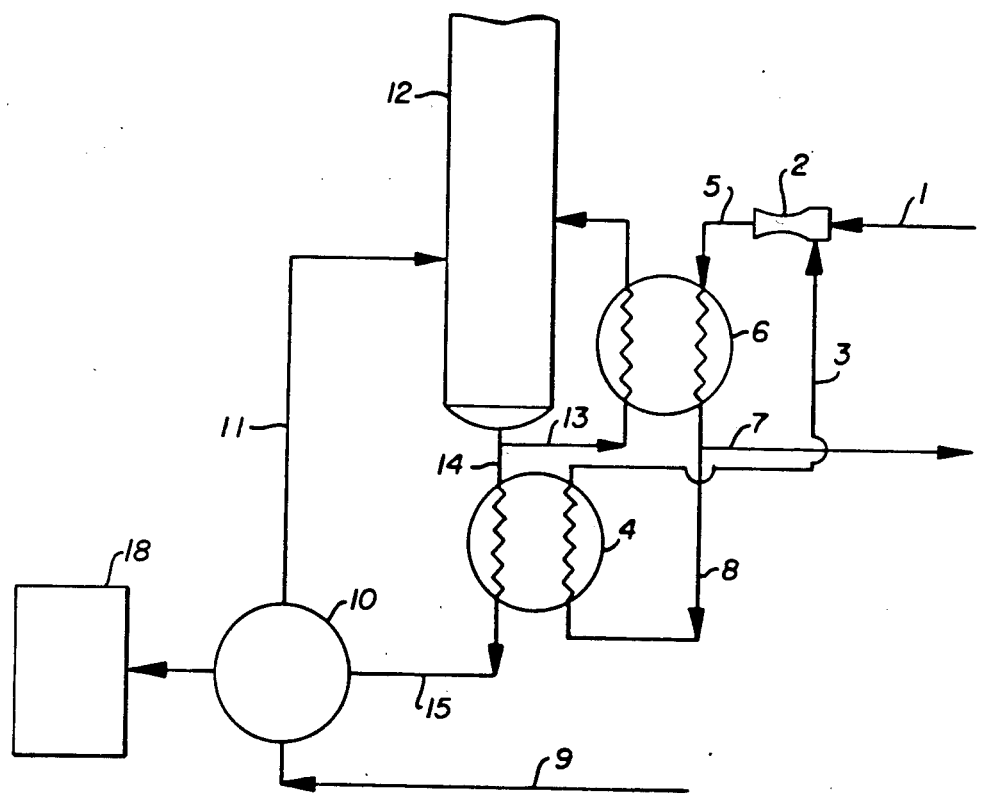

PROCESS FOR THE SEPARATION OF HYDROCARBONS FROM A MIXED FEEDSTOCK

TECHNICAL FIELD

This invention relates to a steam distillation process for the recovery of hydrocarbons from a mixed feedstock.

BACKGROUND ART

The benzene-toluene-$C_8$ aromatic fraction (known and hereinafter referred to as BTX) is now well established as a premier raw material in the manufacture of petrochemicals and as a desirable component in boosting octane ratings in gasoline. Many processes have been proposed for the separation of BTX, e.g., the process proposed in U.S. Pat. No. 3,714,033, which is incorporated by reference herein.

There is an industrial need for BTX, which is available in high proportion, e.g., greater than 30 percent by weight, in a wide variety of hydrocarbon feedstocks such as reformed gasolines; coke oven light oils; and cracked gasolines. These feedstocks also contain both aliphatic and cycloaliphatic hydrocarbons. Since the individual hydrocarbon compounds which make up these feedstocks are well known, they will not be discussed extensively; however, it can be pointed out that the major components of the feedstocks used herein are hydrocarbons with boiling points ranging from 25° C. to 175° C. including straight-chain and branched-chain paraffins and naphthenes, such as n-heptane, isooctane, and methyl cyclohexane, and aromatics such as BTX.

The BTX fraction can include benzene, toluene, the $C_8$ aromatics including ortho-xylene, meta-xylene, para-xylene, and ethyl benzene, and $C_9$ aromatics, which, if present at all, appear in the smallest proportion in relation to the other components.

The solvents used in solvent extraction/steam distillation (stripping) processes for the recovery of BTX are water-miscible organic liquids (at process temperatures) having a boiling point of at least about 200° C. and having a decomposition temperature of at least about 225° C. The term "water-miscible" includes those solvents which are completely miscible over a wide range of temperatures and those solvents which have a high partial miscibility at room temperature since the latter are usually completely miscible at process temperatures. The solvents are also polar and are generally comprised of carbon, hydrogen, and oxygen with some exceptions. Examples of solvents which may be used in the process of this invention are dipropylene glycol, tripropylene glycol, dibutylene glycol, tributylene glycol, ethylene glycol, diethylene glycol, ethylene glycol monomethyl ether, ethylene glycol monoethyl ether, diethylene glycol monomethyl ether, diethylene glycol monoethyl ether, sulfolane, N-methyl pyrrolidone, triethylene glycol, tetraethylene glycol, ethylene glycol diethyl ether, propylene glycol monoethyl ether, pentaethylene glycol, hexamethylene glycol, and mixtures thereof. The preferred group of solvents is the polyalkylene glycols and the preferred solvent is tetraethylene glycol.

Additional solvents, which may be used alone or together, or with the aforementioned solvents are amides such as formamide, acetamide, dimethylformamide, diethylformamide, and dimethylacetamide; amines such as diethylenetriamine and triethylenetetramine; alkanolamines such as monoethanolamine, diethanolamine, and triethanolamine; nitriles such as beta,beta[1]-oxydipionitrile and beta,beta[1]-thiodipropionitrile; phenol and the cresols; the methyl sulfolanes; sulfoxides such as dimethyl sulfoxide and diethyl sulfoxide; lactones such as gamma-propiolactone and gamma-butyrolactone.

The apparatus used in the process both for extraction and distillation is conventional, e.g., an extraction column of the multi-stage reciprocating type containing a plurality of perforated plates centrally mounted on a vertical shaft driven by a motor in an oscillatory manner can be used as well as columns containing pumps with settling zones, sieve trays with upcomers, or even a hollow tube while the distillation can be conducted in a packed, bubble plate, or sieve tray fractionating column. Counter-current flows are utilized in both extraction and distillation columns.

Heat exchangers, decanters, reservoirs, solvent regenerators, condensers, compressors, and pumps as well as various extractors other than the main extractor can also be used to complete the system. The other extractors are preferably single stage mixer-settlers, but can be any of the well known types. Again, all of this apparatus is conventional off-the-shelf equipment commonly used in extraction/distillation processes.

The solvent is used as an aqueous solution containing water in an amount of about 1 percent to about 10 percent by weight based on the weight of the solvent and preferably containing water in an amount of about 2 percent to about 6 percent by weight.

Generally, to accomplish the extraction, the ratio of solvent (exclusive of water) to feedstock in the extractor is in the range of about 4 to about 8 parts by weight of solvent to one part by weight of feedstock. This broad range can be expanded upon where nonpreferred solvents are used. A broad range of about 3 to about 12 parts by weight of solvent to one part by weight of feedstock and a preferred range of about 5 parts to about 7 parts of solvent per part of feedstock can be used successfully for the solvent of preference and other like solvents. In final analysis, however, the ratio is selected by the technician based on experience with the particular feedstock and depends in part upon whether high recovery or high purity is being emphasized.

The reflux to the extraction zone, an important part of the process, is generally made up of about 20 percent to about 50 percent by weight aliphatics having from 5 to 7 carbon atoms and about 50 percent to about 80 percent by weight aromatics, both based on the total weight of the reflux. The ratio of reflux to feedstock in the extraction zone is, generally, maintained in the range of about 0.5 to about 1.5 parts by weight of reflux to one part by weight of feedstock and preferably about 0.5 to about 1.0 part by weight of reflux to one part by weight of feedstock, but, again, is selected by the technician just as the ratio of solvent to feedstock. The reflux aliphatics pass into the extract rather than being taken overhead with the raffinate and are recycled to the extractor from the reflux decanter.

The temperature in the extraction zone is maintained in the range of about 100° C. to about 200° C. and is preferably in the range of about 125° C. to about 150° C., especially for the solvent of preference.

The pressure in the extraction zone is maintained in the range of about 75 psig to about 200 psig. As is well known in the art, however, one selected pressure is not maintained throughout the extraction zone, but, rather, a high pressure within the stated range is present at the bottom of the zone and a low pressure, again within the stated range, is present at the top of the zone with an intermediate pressure in the middle of the zone. The pressures in the zone depend on the design of the equipment and the temperature, both of which are adjusted to maintain the pressure within the stated range.

The temperature at the top of the distillation zone, which, in terms of the apparatus used, may be referred to as a distillation column or stripper, is at the boiling point of the mixture of aromatics present in the zone while the temperature at the bottom of the stripper is generally in the range of about 135° C. to about 200° C.

The pressure at the top of the stripper, an upper flash zone in this case, is in the range of about 20 psig to about 45 psig. In a lower flash zone just beneath the upper flash zone and connected thereto, the pressure is in the range of about zero psig to about 25 psig and is about 10 or 20 psig lower than the pressure in the upper flash zone. The pressure in the rest of the distillation zone is maintained in the range of about 5 psig to about 25 psig with some variation throughout the zone.

The steam or steam/water mixture brought into the bottom of the distillation zone enters at a temperature of about 100° C. to about 150° C. and is under a pressure of about 5 psig to about 25 psig. The total water and/or steam injected into the distillation column is in the range of about 0.1 part to about 0.5 part by weight of water to one part by weight of aromatics in the zone and preferably in the range of about 0.1 part to about 0.3 part by weight of water to one part by weight of aromatics. The water used for the stripping steam is usually called stripping water. The stripping water may or may not be recirculated throughout the process before being recycled to the distillation column. A small amount of water is present in liquid form in the distillation zone dissolved in the solvent.

Typically, in solvent extraction/steam distillation processes, the feedstock is preheated and then introduced to the main extractor at about the middle tray. An aqueous solvent solution (known as lean solvent) enters at the top tray of the extractor and percolates down the column removing aromatics from the feedstock. The raffinate, essentially free of aromatics, leaves the top of the column. Provisions are made for the recovery of solvent and any remaining aromatics from the raffinate as well as the water which is used to wash it. In the lower half of the extractor, the solvent solution of aromatics comes into countercurrent contact with a reflux liquid, which enters the extractor below the bottom tray. The reflux percolates up the lower half of the extractor progressively dissolving in and purifying the solvent solution of aromatics. The extract (known as rich solvent) leaves the bottom of the extractor, is heated in a heat exchanger to a temperature in the range of about 100° C. to about 150° C., and enters the top of the stripper (or distillation zone) at an upper or primary flash chamber. The primary flash chamber is maintained at a pressure in the range of about 10 pounds per square inch gauge (psig) to about 60 psig. Part of the extract flashes on entering the flash chamber and is taken overhead in vapor form at a temperature in the range of about 90° to about 140° C. and at a pressure in the range of about 15 psig to about 55 psig and the other part of the extact passes as a liquid into a lower or secondary flash chamber. Again, part of the extract, flashes overhead and the balance of the extract (at least about 80 percent by weight) percolates down the column into the fractionation zone where it comes into countercurrent contact with the stripping vapors, i.e., steam, and more vapors are generated. A part of the vapors rises to the top of the column where it mixes with flash vapors from the primary and secondary flash chambers to form the overhead distillate. The overhead distillate vapors are introduced into a reflux condenser where the vapors are condensed and passed into a decanter. Here, a hydrocarbon reflux phase is separated from a first water phase. The reflux is recycled to the extractor and the first water phase is combined with the second water phase from the side-cut distillate for use as stripping water. After the rich solvent descends about halfway down the column, it becomes essentially free of aliphatics. At this point, a vapor side-cut distillate (or extract) is removed. The side-cut distillate is condensed and separated in a decanter into its aromatics and solvent/water components, the aromatics (or extract phase) being recovered for further distribution and separation and the solvent and water (the second water phase) being recycled into the system. As noted above, stripping water from the side-cut distillate and other water from the system are returned to the bottom of the stripper as steam or a steam/water mixture. The bulk of the solvent and water leaves the bottom of the stripper. A portion of this solution is directed to a reboiler where it is vaporized and then returned to a point below the bottom tray of the stripper to provide heat therefor. The balance of the solvent/water solution is recycled to the top tray of the main extractor.

There are many specific variations of the above process, each of which seeks either to reduce apparatus requirements, i.e., capital expenditure, or energy consumption, or make more effective use of process components while meeting purity specifications.

DISCLOSURE OF THE INVENTION

An objective of this invention is to reduce energy consumption with a nominal increase in capital expenditure.

Other objectives and advantages will become apparent hereinafter.

According to the invention, an improvement has been found in a solvent extraction/steam distillation process for the recovery of aromatic hydrocarbons.

The improvement comprises (a) introducing high pressure steam into a steam ejector; (b) passing the steam from step (a) to a first heat exchanger where it exchanges heat with cooler lean solvent coming from the bottom of the distillation column and is condensed; (c) returning the lean solvent from step (b) to the bottom of the distillation column; (d) passing part of the condensate from step (b) to a second heat exchanger where it exchanges heat with the warmer lean solvent coming from the bottom of the distillation column, cooling the lean solvent and vaporizing the condensate; and (e) passing the vapor from step (d) to the steam ejector in step (a).

BRIEF DESCRIPTION OF THE DRAWING

The sole FIGURE is a schematic flow diagram of an illustrative embodiment of the subject invention.

DETAILED DESCRIPTION

The main extractor, feedstock, solvent, temperatures, and pressures are as described above except as noted.

Water is converted to high pressure steam with a temperature in the range of about 200° C. to about 250° C. and a pressure in the range of about 200 to about 600 psig. This steam is used to drive steam ejector 2 and heat exchanger (or reboiler) 6. The water introduced into line 9, below, is initially obtained from recirculation within the process.

Referring to the drawing:

The high pressure steam passes along line 1 to steam ejector 2, providing the driving force therefor. Steam at a temperature of about 115° C. to about 170° C. and a pressure of about 10 psig to about 100 psig enters steam ejector 2 along line 3 from heat exchanger 4. Steam ejector 2 pumps the steam from line 3 along line 5 at a temperature of about 150° C. to about 200° C. and a pressure of about 50 psig to about 200 psig into heat exchanger 6 where it is condensed. The condensate is then divided. One part of the condensate passes along line 7 back to a steam generator and returns as high pressure steam in line 1. Another part of the condensate passes through line 8 to heat exchanger 4 where it is vaporized at a lower pressure to a temperature in the range of about 115° C. to about 170° C. and a pressure in the range of about 10 psig to about 100 psig. The low pressure vapor then is taken along line 3 to steam ejector 2, as noted above, where it joins the line 3 steam and is compressed.

In a preferred mode, water is taken along line 9 to lean solvent/water heat exchanger 10. Here, the water is vaporized, reaching a temperature in the range of about 100° C. to about 125° C. and a pressure in the range of about 0 psig to about 20 psig. This vapor passes along line 11 into the bottom of distillation column 12 where it is utilized as stripping steam. The temperature at the bottom of the distillation (stripping) column 12 is in the range of about 130° C. to about 160° C. and the pressure is in the range of about 2 psig to about 15 psig. As an alternative, a rich solvent heat exchanger can be used in the conventional manner to provide stripping steam.

Lean solvent leaves the bottom of distillation column 12, part of it passing through line 13, and the balance through line 14. The line 13 lean solvent enters heat exchanger 6 where it is brought to temperature and returned to the bottom of distillation column 12. At the bottom of distillation column 12, reboiler vapors assist line 11 stripping vapors in effecting the distillation.

The balance of the lean solvent, at a temperature in the range of about 130° C. to about 160° C., is taken along line 14 into heat exchanger 4 where it vaporizes the condensate. The lean solvent, at a temperate in the range of about 130° C. to about 150° C., then continues along line 15 into heat exchanger 10 where it vaporizes the water from line 9 and, then, at a temperature in the range of about 110° C. to about 140° C., is recycled to the top of extractor 18.

In the present case, the lean solvent is responsible for the vaporization of condensate in heat exchanger 4 and preferably for the stripping water in heat exchanger 10. This is achieved by extracting heat twice from the lean solvent in the successive heat exchangers 4 and 10. In doing so, a good deal of heat is extracted from the lean solvent, lowering its temperature. The cooler lean solvent, in turn, is much more selective for the aromatic fraction and, of course, less selective for the non-aromatic fraction. This causes a reduction in the reflux to feed ratio, and, consequently, a reduction in heat duty. The lower reflux to feed ratio can result in an increase in the recovery of aromatics, but, if this is not an objective, a reduction in solvent to feed ratio can be achieved.

The advantages of subject process are summarized as follows:

1. High energy savings. This is due to lower reflux to feed ratios and/or lower solvent recirculation rates.
2. Steam ejectors are inexpensive as compared to the usual compressors.
3. The capital investment is not much higher than that of a system using a rich solvent/stripping water heat exchanger since only one additional heat exchanger is required.

The invention is illustrated by the following example (percentages and ratios are by weight):

The process described above and in the drawing is carried out in the preferred mode. The feedstock is characterized as a reformate containing about 42.53 percent BTX.

The composition of the feed is as follows:

| Hydrocarbon | wt. % |
|---|---|
| Benzene | 11.17 |
| Toluene | 29.45 |
| Xylene | 1.91 |
| n-Pentane | 8.54 |
| n-Hexane | 17.20 |
| Heptane | 18.29 |
| Octane | 10.13 |
| Cyclohexane | 0.78 |
| Methylcyclopentane | 1.28 |
| Methylcyclohexane | 1.25 |
| | 100.00% |

The lean solvent solution contains about 94 percent tetraethylene glycol and about 6 percent water.

The operating conditions and results are as follows:

| | |
|---|---|
| temperature of rich solvent entering stripper 12 | 120° C. |
| pressure in primary flash chamber | 35 psig |
| temperature of primary flash vapors | 116° C. |
| temperature of side-cut distillate (extract) vapors | 121° C. |
| pressure of side-cut distillate (extract) vapors | 7 psig |
| temperature in stripper 12 (bottom) | 154° C. |
| pressure in stripper 12 (bottom) | 9 psig |
| temperature of water vapors from steam ejector 2 (line 5) | 170° C. |
| pressure of water vapors from steam ejector 2 (line 5) | 100 psig |
| pressure of motive steam in line 1 | 400 psig |
| temperature of condensate exiting heat exhanger 6 | 170° C. (approx). |
| temperature of condensate vapors exiting heat exchanger 4 | 142° C. |
| pressure of condensate vapors exiting heat exchanger 4 | 41 psig |
| feedstock rate (pounds per hour) | 265,917 |
| solvent solution to feedstock ratio | 6.42 |
| reflux to feedstock ratio | 0.59 |
| stripping water rate (pounds per hour) | 35,398 |
| side-cut distillate (extract) vapors (pounds per hour) | 113,000 |
| raffinate rate (pounds per hour) | 152,822 |
| reflux rate (pounds per hour) | 157,690 |
| lean solvent rate (pounds per hour) | 1,707,330 |
| lean solvent temperature in line 13 | 154° C. |
| lean solvent temperature in line 15 | 147° C. |
| lean solvent temperature in line 16 | 127° C. |
| lean solvent water content (percent by weight) | 5.2 |
| water vaporized in heat | 100 |

-continued

| | |
|---|---|
| exchanger 10 (percent by weight) | |
| Recoveries, i.e., percent of recovery based on amount in feedstock: | |
| benzene | 100.00 |
| toluene | 99.90 |
| xylene | 98.39 |
| impurities in extract (parts per million by weight) | 599 |
| reboiler duty ($10^6$ BTU's per hour) | 88.2 |
| estimated energy saved ($10^6$ BTU's per hour) | 14.8 |
| estimated energy reduction (percent) | 14.4 |
| heat duty in BTU's per pound of BTX | 781 |

Note: Energy savings and percentage reduction are based on a comparison with a process run using the same steps and conditions except that steam ejector 2 and heat exchanger 4 are not used. Instead, a rich solvent/stripping water heat exchanger is used to provide heat to vaporize the stripping water in place of lean solvent heat exchanger 10.

We claim:

1. In a combination solvent extraction-steam distillation process for the recovery of aromatic hydrocarbons, the improvement comprising (a) introducing high pressure steam into a steam ejector;

(b) passing the steam from step (a) to a first heat exchanger where it exchanges heat with lean solvent coming from the bottom of a distillation column, which lean solvent has a temperature which is cooler than the steam temperature, and is condensed;

(c) returning the lean solvent from step (b) to the bottom of the distillation column;

(d) passing part of the condensate from step (b) to a second heat exchanger where it exchanges heat with the lean solvent coming from the bottom of the distillation column which lean solvent has a temperature which is warmer than the condensate temperature, cooling the lean solvent and vaporizing the condensate; and (e) passing the vapor from step (d) to the steam ejector in step (a).

2. The process defined in claim 1 wherein the following additional steps are carried out:

(f) passing a water stream to a third heat exchanger where it exchanges heat with lean solvent from step (d), which lean solvent has a temperature which is warmer than the water stream temperature, and is vaporized;

(g) passing the vapor from step (f) to the bottom of the distillation column; and (h) passing the lean solvent from step (f) to the top of an extractor.

* * * * *